US009072471B2

(12) United States Patent
Kato et al.

(10) Patent No.: US 9,072,471 B2
(45) Date of Patent: Jul. 7, 2015

(54) PORTABLE ULTRASOUND DIAGNOSIS APPARATUS

(71) Applicants: Kabushiki Kaisha Toshiba, Minato-ku (JP); Toshiba Medical Systems Corporation, Otawara-shi (JP)

(72) Inventors: Tooru Kato, Nasushiobara (JP); Mikihito Hayashi, Otawara (JP); Kanta Kobuchi, Otawara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/035,017

(22) Filed: Sep. 24, 2013

(65) Prior Publication Data

US 2014/0024939 A1 Jan. 23, 2014

Related U.S. Application Data

(63) Continuation of application No. PCT/JP2012/080589, filed on Nov. 27, 2012.

(30) Foreign Application Priority Data

Nov. 28, 2011 (JP) .................................. 2011-259638

(51) Int. Cl.
*A61B 8/14* (2006.01)
*A61B 8/08* (2006.01)
*A61B 8/00* (2006.01)

(52) U.S. Cl.
CPC ... *A61B 8/14* (2013.01); *A61B 8/08* (2013.01); *A61B 8/4427* (2013.01); *A61B 8/462* (2013.01);

(Continued)

(58) Field of Classification Search
CPC ............ A61B 8/006; A61B 8/54; A61B 8/56; A61B 8/585; A61B 8/00; A61B 8/4427; A61B 8/463; A61B 8/4433; A61B 8/4411; A61B 8/465; G01S 7/52053; G01S 7/52074; G06F 1/1632
See application file for complete search history.

(56) References Cited

U.S. PATENT DOCUMENTS 5,590,658 A 1/1997 Chiang et al.
5,690,114 A 11/1997 Chiang et al.
(Continued)

FOREIGN PATENT DOCUMENTS

JP 10-234731 9/1998
JP 11-508461 7/1999
(Continued)

OTHER PUBLICATIONS

International Search Report issued on Feb. 26, 2013 for PCT/JP2012/080589 filed on Nov. 27, 2012 with English Translation.
(Continued)

*Primary Examiner* — Elmer Chao
(74) *Attorney, Agent, or Firm* — Oblon, McClelland, Maier & Neustadt, L.L.P.

(57) ABSTRACT

A portable ultrasound diagnosis apparatus includes: an ultrasound probe that transmits and receives an ultrasound wave to and from a subject; a processing unit being connected to the ultrasound probe and including a generating unit that generates image data of the subject on the basis of an ultrasound signal received by the ultrasound probe; a display controlling unit that exercises control so as to cause the image data to be displayed by an information terminal being connected to the processing unit and having a display unit; and an identifying unit that performs an identifying process on the basis of identification information of the information terminal. The display controlling unit exercises control so that the information terminal displays a diagnosis image area while varying the size thereof relative to the size of the display unit, in accordance with a result of the identifying process by the identifying unit.

12 Claims, 16 Drawing Sheets

(52) U.S. Cl.
CPC ............... *A61B 8/465* (2013.01); *A61B 8/461* (2013.01); *A61B 8/5292* (2013.01); *A61B 8/54* (2013.01); *A61B 8/56* (2013.01); *A61B 8/585* (2013.01); *A61B 8/565* (2013.01)

(56) References Cited

U.S. PATENT DOCUMENTS

| | | | |
|---|---|---|---|
| 5,839,442 | A | 11/1998 | Chiang et al. |
| 5,904,652 | A | 5/1999 | Gilbert et al. |
| 5,957,846 | A | 9/1999 | Chiang et al. |
| 5,964,709 | A | 10/1999 | Chiang et al. |
| 6,364,839 | B1 | 4/2002 | Little et al. |
| 6,447,451 | B1 | 9/2002 | Wing et al. |
| 7,115,093 | B2 | 10/2006 | Halmann et al. |
| 7,534,211 | B2 | 5/2009 | Hwang et al. |
| 8,088,071 | B2 | 1/2012 | Hwang et al. |
| 8,241,217 | B2 | 8/2012 | Chiang et al. |
| 8,469,893 | B2 | 6/2013 | Chiang et al. |
| 8,535,227 | B2 | 9/2013 | Halmann et al. |
| 2002/0143256 | A1 | 10/2002 | Wing et al. |
| 2003/0028113 | A1 | 2/2003 | Gilbert et al. |
| 2003/0071829 | A1* | 4/2003 | Bodicker et al. ............ 345/619 |
| 2004/0254763 | A1* | 12/2004 | Sakai et al. ................. 702/184 |
| 2008/0161688 | A1 | 7/2008 | Poland |
| 2008/0294046 | A1 | 11/2008 | Chiang et al. |
| 2010/0004535 | A1 | 1/2010 | Song et al. |

FOREIGN PATENT DOCUMENTS

| | | |
|---|---|---|
| JP | 2001-357134 | 12/2001 |
| JP | 2002-542870 | 12/2002 |
| JP | 2003-190159 | 7/2003 |
| JP | 2006-26256 | 2/2006 |
| JP | 2006-518254 | 8/2006 |
| JP | 2008-536601 | 9/2008 |
| JP | 2009-153917 | 7/2009 |
| JP | 2010-12227 | 1/2010 |

OTHER PUBLICATIONS

International Written Opinion issued on Feb. 26, 2013 for PCT/JP2012/080589 filed on Nov. 27, 2012.

* cited by examiner

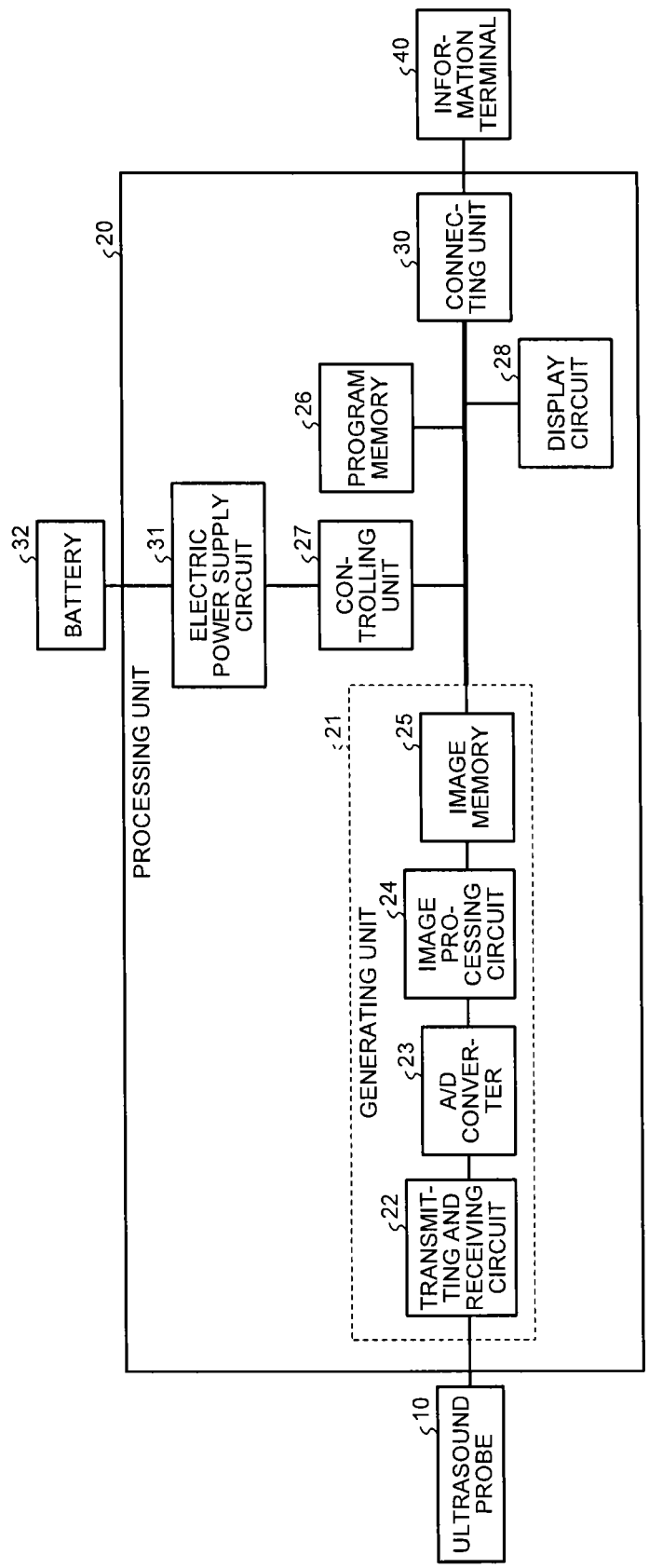

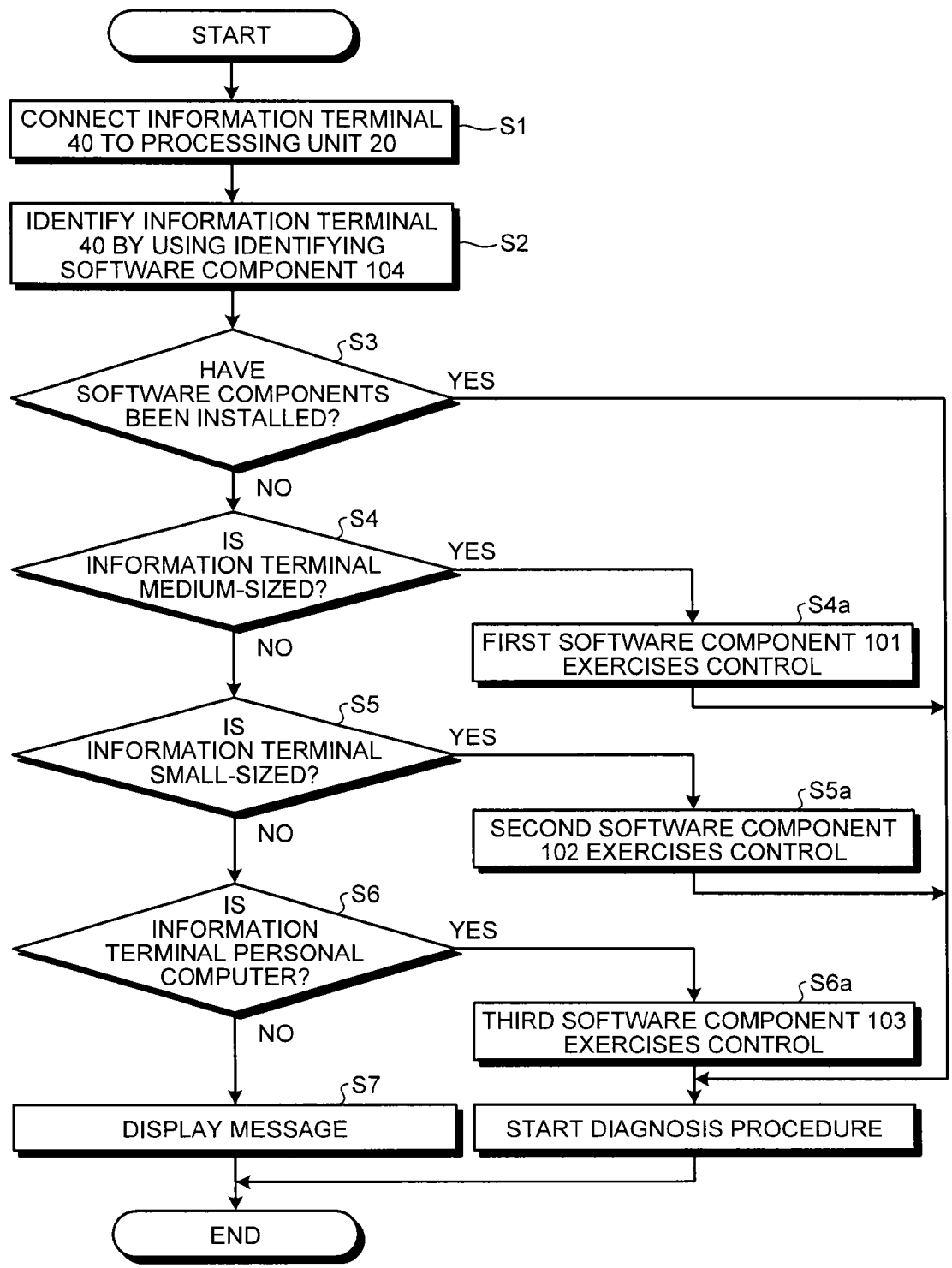

FIG.6C
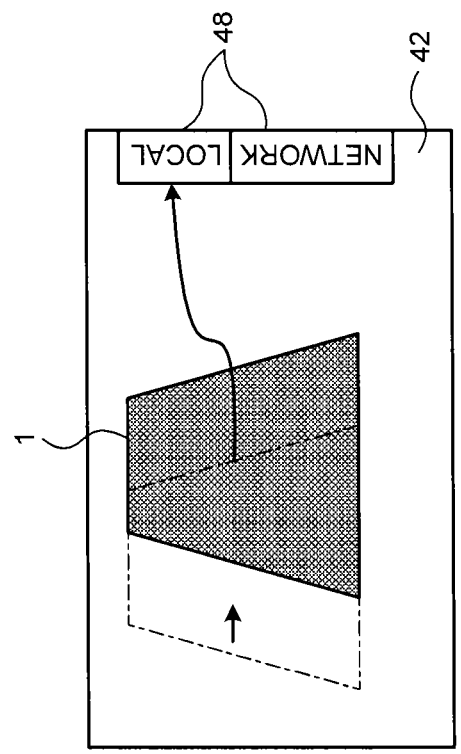
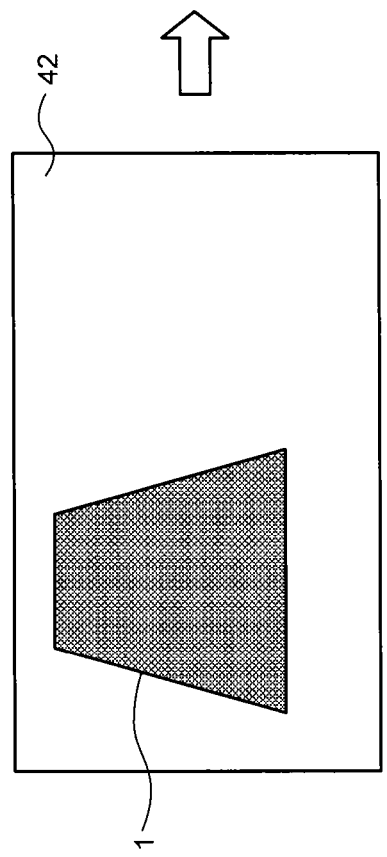

PORTABLE ULTRASOUND DIAGNOSIS APPARATUS

CROSS-REFERENCE TO RELATED APPLICATION(S)

This application is a continuation of International Application No. PCT/JP2012/080589, filed on Nov. 27, 2012 which claims the benefit of priority of the prior Japanese Patent Application No. 2011-259638, filed on Nov. 28, 2011, the entire contents of which are incorporated herein by reference.

FIELD

Embodiments described herein relate generally to a portable ultrasound diagnosis apparatus.

BACKGROUND

In recent years, there has been a demand for further technical development in hand-held-type ultrasound diagnosis apparatuses due to the importance of home medical care. Being compact and having excellent portability, hand-held-type ultrasound diagnosis apparatuses make it possible to perform a diagnosis procedure regardless of location. Thus, the convenience of hand-held-type ultrasound diagnosis apparatuses is recognized as enabling medical doctors to visit patients' residences and perform diagnosis procedures. To realize the portability of the apparatuses, however, the size of the monitor screens is limited.

As the apparatuses become more compact, the operating units also become relatively smaller, which degrades the operability. The size of the monitor screens (visibility) and the easiness to carry the monitors (portability) are in a relationship of antinomies, and there is an ongoing demand for fulfilling the requirements for both.

To cope with this situation, although it is possible to use a television (TV), which is usually available in any household, as a monitor, the diagnosis procedures in that situation would need to be performed only in the vicinity of the TV, and it would be difficult to perform the diagnosis procedures in desired locations such as on a bed.

In addition, information terminals such as smartphones and tablet terminals have become significantly popular in recent years, and different companies offer different types of products. Because of intuitive operations, those information terminals are easy for everyone to use. Further, because of communication functions, those information terminals are also capable of transmitting and receiving data. Thus, those information terminals are very much expected to be useful in the medical field. However, the size of the monitor screens of the information terminals that are in practical use vary greatly, from small ones such as those on portable phones to large ones close to the size of a TV screen. When a diagnosis image needs to be displayed on an information terminal for use in the medical field, the display size of the diagnosis image will change so as to fit the size of the monitor screen, which varies greatly. Thus, in some situations, the diagnosis image may be displayed in a size that is not suitable for a diagnosis procedure.

BRIEF DESCRIPTION OF THE DRAWINGS

FIG. 2A and FIG. 2B are block diagrams of an overall configuration according to the first embodiment;

FIG. 4 is a flowchart illustrating a flow of a series of operations according to the first embodiment;

FIG. 6A, FIG. 6B and FIG. 6C are schematic drawings of an exemplary diagnosis screen on a display unit controlled by a second software component according to the first embodiment;

DETAILED DESCRIPTION

A portable ultrasound diagnosis apparatus according to an embodiment includes an ultrasound probe, a processing unit, a display controlling unit, and an identifying unit. The ultrasound probe is configured to transmit and receive an ultrasound wave to and from a subject. The processing unit is connected to the ultrasound probe and includes a generating unit configured to generate image data of the subject on a basis of an ultrasound signal received by the ultrasound probe. The display controlling unit is configured to exercise control so as to cause the image data to be displayed by an information terminal being connected to the processing unit and having a display unit. The identifying unit is configured to perform an identifying process on a basis of identification information of the information terminal. The display controlling unit exercises control so that the information terminal displays a diagnosis image area while varying a size thereof relative to a size of the display unit, in accordance with a result of the identifying process by the identifying unit.

Exemplary embodiments for implementing the disclosure herein will be explained below.

An overview of a portable ultrasound diagnosis apparatus according to a first embodiment will be explained, with reference to FIG. 1.

Figure 1:
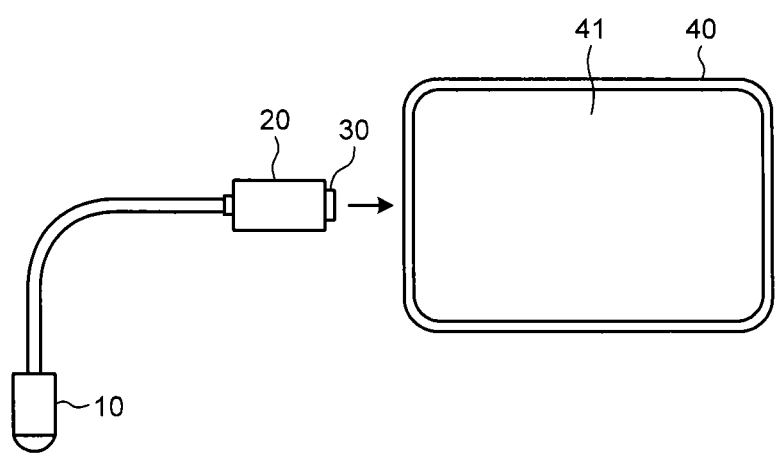
FIG. 1 is a schematic drawing of an overall configuration according to a first embodiment.
Figure 2B:
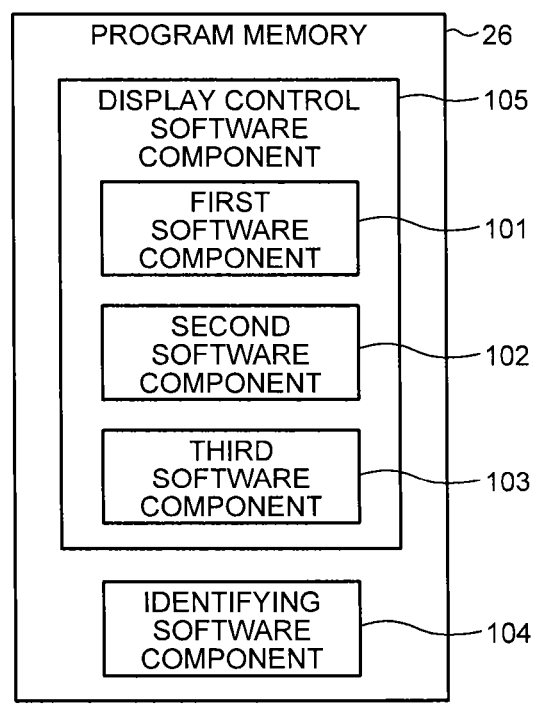

FIG. 1 is a schematic drawing for explaining a relationship between a portable ultrasound diagnosis apparatus and an information terminal 40 according to a first embodiment. A processing unit 20 has an ultrasound probe 10 connected thereto and is provided with a connecting unit 30 connectable to the information terminal 40. On the basis of information about the information terminal 40 connected to the processing unit 20, the processing unit 20 exercises control in accordance with the type of the information terminal 40. Further, the processing unit 20 generates image data from signals obtained from the ultrasound probe 10 and exercises control so as to cause the image data and operation buttons 43 to be optimally displayed on a display unit 41 with which the information terminal 40 is provided. FIG. 2A is a block diagram for explaining a relationship among those functional units.

The ultrasound probe 10 is configured to generate an ultrasound wave by causing an ultrasound transducer element provided at a tip end thereof to mechanically vibrate and to emit the ultrasound wave toward a subject. The emitted ultrasound wave propagates through the subject's body and is repeatedly reflected on a surface of discontinuity of acoustic impedances during the propagation, so that reflected waves are received by the ultrasound probe 10.

The processing unit 20 includes: a generating unit 21 configured to generate an ultrasound image; the connecting unit 30 connectable to the information terminal 40; and an electric power supply circuit 31 configured to supply electric power from a battery 32 (not shown in FIG. 1) connected to the processing unit 20. Further, the processing unit 20 includes: a storage unit such as a program memory 26 provided with software used for causing the ultrasound image generated by the generating unit 21 to be displayed on the display unit 41; and a controlling unit 27 configured to exercise control for, for example, changing an image mode and having data written to a memory. Further, the processing unit 20 also includes a display circuit 28 configured to cause various types of ultrasound images to be displayed on the display unit 41, according to an instruction from a display control software component 105 provided in the controlling unit 27.

Further, the processing unit 20 also includes one or more minimum operation switches or a monitor (not shown) to be used for controlling the information terminal 40 connected thereto. For example, the operation switches provided for the processing unit 20 serve as an electric power switch for switching between an activated state and a terminated state of the processing unit 20 and as a connection switch for instructing a connecting process between the connecting unit 30 and the information terminal 40. In this situation, the electric power supply for driving the processing unit 20 and the ultrasound probe 10 may be obtained from the battery 32 directly connected to the processing unit 20 or may be obtained from the information terminal 40 while the information terminal 40 and the connecting unit 30 are physically connected to each other.

The generating unit 21 includes a transmitting and receiving circuit 22, an Analog/Digital (A/D) converter 23, an image processing circuit 24, and an image memory 25. The transmitting and receiving circuit 22 is configured to transmit and receive the ultrasound waves from the ultrasound probe 10. The A/D converter 23 is configured to convert ultrasound signals received by the ultrasound probe 10 into digital signals. After that, the image processing circuit 24 processes the digital signals from the A/D converter 23 and generates image data in various modes such as a B-mode, an M-mode, a Doppler mode, and a color Doppler mode.

The program memory 26 has stored therein (FIG. 2B): a first software component 101, a second software component 102, and a third software component 103 configured to exercise screen control corresponding to the information terminal 40 being connected; an identifying software component 104 configured to identify the information about the information terminal 40; and the display control software component 105 configured to control display of images. The image memory 25 is configured to store therein the image data generated by the generating unit 21 and to transmit the image data to the controlling unit 27.

The connecting unit 30 is connectable to an external terminal such as the information terminal 40 and includes a physically-connectable connector or a wireless means. When having received an instruction from the controlling unit 27, the connecting unit 30 transmits the image data read from the image memory 25 to the information terminal 40 or transmits one of the first to the third software components read from the program memory 26 to the information terminal.

The information terminal 40 is a device that has the display unit 41 and may be a medium-sized information terminal such as a tablet terminal, a small-sized information terminal such as a smartphone, or a personal computer. Each device is identified by the size of the display unit 41 or the like. Further, the information terminal 40 has a communication function to enable communication with an external source. It is preferable if the information terminal 40 has a wireless function realized by an infrared ray or the like.

The controlling unit 27 includes a Central Processing Unit (CPU) and is configured to control the constituent elements by executing the software components stored in the program memory 26.

The identifying software component 104 is configured to obtain identification information corresponding to the type of the information terminal 40 and to specify a software component to be executed from among the first to the third software components included in the display control software component 105 stored in the program memory 26, on the basis of the obtained identification information. The identifying software component 104 is configured to specify the first software component 101 if the information terminal 40 is a medium-sized information terminal, to specify the second software component 102 if the information terminal 40 is a small-sized information terminal, and to specify the third software component 103 if the information terminal 40 is a personal computer.

The identification information of the information terminal 40 identified by the identifying software component 104 is, for example, information about the size of the display unit 41 provided for the information terminal 40, information related to the model of the information terminal 40 (e.g., a model number), or information indicating whether an operating unit (e.g., a touch panel and/or a keyboard, or a pointing device) is present or not. The size may be expressed as the actual dimensions of the display unit 41 or as the number of pixels. The identification information may be obtained by extracting information from the information terminal 40 through communication with the information terminal 40 by causing the processing unit 20 to execute the identifying software component 104 or may be obtained by using the communication function of the information terminal 40. If the obtained identification information indicates a size, the identifying software component 104 classifies the connected information terminal 40 by comparing the size with a threshold value that is stored in the identifying software component 104 in advance and is used for identifying the size. The identifying software component 104 thus selects the software component to be specified, on the basis of the classification.

The identifying software component 104 according to the first embodiment classifies the information terminal 40 connected to the processing unit 20 as one of the three types of information terminals, i.e., a medium-sized information terminal, a small-sized information terminal, or a personal computer, and specifies the software component corresponding to the classification. More specifically, for example, the identifying software component 104 first judges whether the information terminal 40 has a touch panel. Subsequently, the identifying software component 104 judges, with respect to the size of the display unit 41 obtained by the identifying software component 104, whether the resolution is equal to or higher than 640×480 or not. If the information terminal 40 has a touch panel and the resolution is equal to or higher than 640×480, the identifying software component 104 determines that the information terminal 40 is a medium-sized information terminal (explained later). If the resolution is lower than 640×480, the identifying software component 104 determines that the information terminal 40 is a small-sized information terminal.

Further, if the resolution of the display unit 41 is equal to or higher than 640×480, while the information terminal 40 has no touch panel, but has an operation function provided with a keyboard and/or a pointing device, the identifying software component 104 determines that the information terminal 40 is a personal computer, and not a medium-sized information terminal. When having determined the classification of the information terminal 40 in this manner, the identifying software component 104 specifies the software component that matches the determined classification.

The identifying software component 104 may be included in the controlling unit 27.

The display control software component 105 is configured to control the image processing circuit 24 that changes the mode of the image data into one of the modes selected from among the B-mode, the M-mode, the Doppler mode, the color Doppler mode, and the like and is configured to cause the image data transmitted from the image memory 25 to be displayed by the information terminal 40. Further, the display control software component 105 is configured to cause operation buttons used for changing the display and storing images to be displayed on the display unit 41 of the information terminal 40. Further, the display control software component 105 selects and executes the one of the software components specified by the identifying software component 104 from among the first to the third software components.

The first software component 101 controls display/operation systems when the information terminal 40 is a medium-sized information terminal. The display unit 41 of the information terminal 40 is provided with the operation buttons used for changing the mode of the image data, changing the display, and storing images.

The second software component 102 controls display/operation systems when the information terminal 40 is a small-sized information terminal. Because the display screen is smaller than the display screen controlled by the first software component 101, the second software component 102 displays, on the display unit 41 of the information terminal 40, only required minimum operation buttons that are in a smaller quantity than the quantity of the operation buttons displayed by the first software component 101.

The third software component 103 controls display/operation systems when the information terminal 40 is an information processing terminal such as a personal computer that has the display unit 41 of which the size is equal to or larger than the display unit 41 of a medium-sized information terminal and is also provided with a keyboard and a pointing device used for controlling the position of a cursor. Because a personal computer is provided with a keyboard, the text input screen can be simpler than those controlled by the first software component 101 and the second software component 102. Further, because inputs are made through the keyboard and not through a touch panel, the pointing device is used for controlling the cursor and the like during a diagnosis procedure.

In this situation, as for the medium-sized information terminal according to the first embodiment, the display unit 41 of the information terminal provided with the touch panel is larger than the display unit of a portable phone, and the weight and the shape thereof are suitable for carrying the information terminal. The resolution of the display unit 41 is assumed to exceed 640×480 pixels, which is commonly used as a resolution level of ultrasound images, for example. In contrast, the display unit 41 of a small-sized information terminal is smaller than that of a medium-sized information terminal and is approximately the same size as the display unit of a portable phone, for example. Further, the display unit 41 of a small-sized information terminal is assumed to have a touch panel installed therein, like the display unit of a medium-sized information terminal. Further, according to the first embodiment, the information terminal 40 is not necessarily required to have a telephone function.

The first software component 101, the second software component 102, and the third software component 103 according to the first embodiment do not necessarily have to be independent of each other. When not independent, the software components share one or more functions such as a basic control function for displaying a diagnosis image, for example.

Figure 3A:
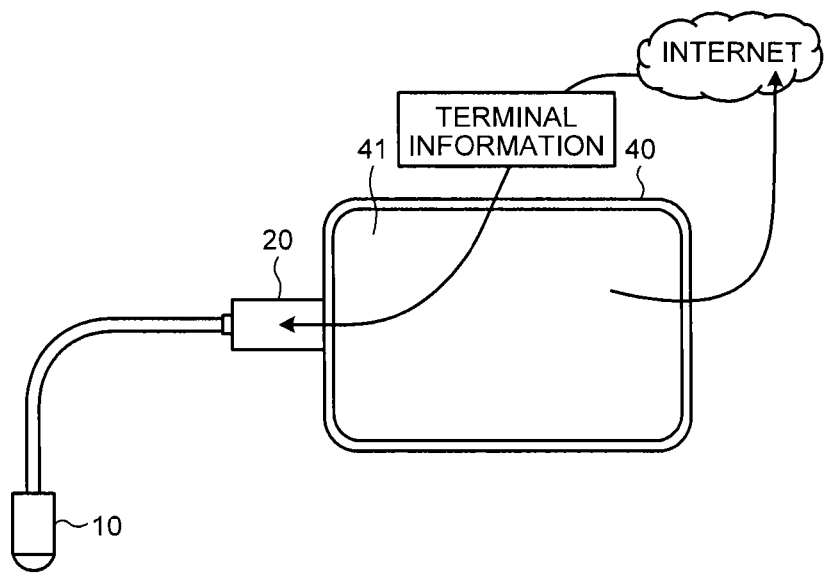
FIG. 3A and FIG. 3B are schematic drawings of a method for identifying an information terminal according to the first embodiment.
Figure 3B:
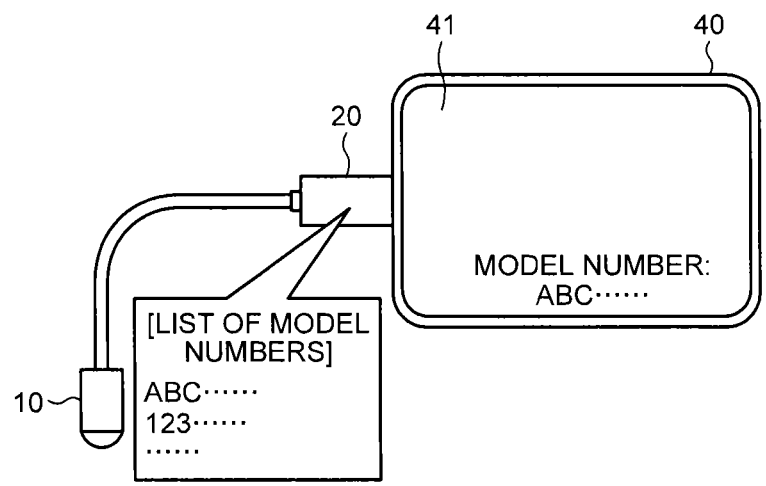

FIGS. 3A and 3B are conceptual drawings of examples of identifying the information terminal 40.

As shown in FIG. 3A, the processing unit 20 accesses the Internet via the communication function of the information terminal 40 and obtains the identification information of the information terminal 40 from an external storage device (not shown) connected to the Internet. For example, the external storage device stores therein information associating model numbers with sizes of the display unit 41. The processing unit 20 recognizes the size of the information terminal 40 by obtaining the model number of the information terminal 40 from a memory of the information terminal 40 and further obtaining the information about the size corresponding to the model number from the external storage device. The processing unit 20 obtains the identification information of the information terminal 40 through the communication function provided on the information terminal 40 side. The identification information is, as explained above, the information regarding the size and the operating unit of the display unit 41, for example. The identifying software component 104 classifies the information terminal 40 according to the size and the type of the operation function of the display unit 41. Alternatively, another arrangement is also acceptable in which, as shown in FIG. 3B, correspondence information between model numbers of the information terminal 40 connectable to the processing unit 20 and the classification is stored on the processing unit 20 side in advance, so as to identify the information terminal 40 by referring to the model number of the information terminal 40 being connected.

Next, an operation of the portable ultrasound diagnosis apparatus according to the first embodiment will be explained.

FIG. 4 is a flowchart according to the first embodiment.

At step S1, the operator connects the information terminal 40 to the processing unit 20. The information terminal 40 may directly be connected to the connecting unit 30 of the processing unit 20. Alternatively, if the information terminal 40 includes a wireless means, the operator operates the processing unit 20 or the information terminal 40 so as to start wireless communication.

At step S2, the identifying software component 104 included in the processing unit 20 obtains the identification information of the information terminal 40, which is connected to the processing unit 20 as a result of step S1.

At step S3, on the basis of the identification information obtained at step S2, the identifying software component 104 judges whether the information terminal 40 connected to the processing unit 20 has already installed therein the first to the third software components (explained later) or other software components used for controlling the display/operation system. If the software components have been installed (step S3: Yes), because there is no need to exercise control from the processing unit 20 side, the installed software component is run so as to control the display/operation system, and the process proceeds to the diagnosis procedure. If the software components have not been installed (step S3: No), the process proceeds to step S4.

At step S4, on the basis of the information obtained at step S2, the identifying software component 104 judges whether the information terminal 40 is a medium-sized information terminal by determining the size of the display unit 41 of the information terminal 40 connected to the processing unit 20 and judging whether a touch panel is provided or not that can be used for performing an operation on a diagnosis image 1 displayed on the display unit 41. If the information terminal 40 is a medium-sized information terminal (step S4: Yes), the process proceeds to step S4a. If the information terminal 40 is not a medium-sized information terminal, the process proceeds to step S5. In this situation, for example, if the resolution of the display unit 41 is equal to or higher than 640×480, and also, a touch panel is provided, as mentioned above, the identifying software component 104 determines that the information terminal 40 is a medium-sized information terminal.

At step S4a, the identifying software component 104 specifies the first software component 101. On the basis of the specified result, the display control software component 105 executes the first software component 101. The first software component 101 thus controls the display/operation system of the information terminal 40 connected to the processing unit 20, and the process proceeds to the diagnosis procedure.

At step S5, on the basis of the information obtained at step S2, the identifying software component 104 judges whether the information terminal 40 is a small-sized information terminal by determining the size of the display unit 41 of the information terminal 40 connected to the processing unit 20 and judging whether a touch panel is provided or not that can be used for performing an operation on the diagnosis image 1 displayed on the display unit 41. If the information terminal 40 is a small-sized information terminal (step S5: Yes), the process proceeds to step S5a. If the information terminal 40 is not a small-sized information terminal (step S5: No), the process proceeds to step S6. In this situation, for example, if the resolution of the display unit 41 is lower than 640×480, and also, a touch panel is provided, as mentioned above, the identifying software component 104 determines that the information terminal 40 is a small-sized information terminal.

At step S5a, the identifying software component 104 specifies the second software component 102. On the basis of the specified result, the display control software component 105 executes the second software component 102. The second software component 102 thus controls the display/operation system of the information terminal 40 connected to the processing unit 20, and the process proceeds to the diagnosis procedure.

At step S6, on the basis of the information obtained at step S2 indicating whether a touch panel and/or a keyboard or a pointing device is provided, the identifying software component 104 checks to see whether the information terminal 40 is a personal computer. If the information terminal 40 is a personal computer (step S6: Yes), the process proceeds to step S6a. If the information terminal 40 is not a personal computer (step S6: No), the process proceeds to step S7. In this situation, if the information terminal 40 has no touch panel, but has a pointing device, the information terminal 40 is determined to be a personal computer.

At step S6a, the identifying software component 104 specifies the third software component 103. On the basis of the specified result, the display control software component 105 executes the third software component 103. The third software component 103 thus controls the display/operation system of the information terminal 40 connected to the processing unit 20, and the process proceeds to the diagnosis procedure.

At step S7, the display control software component 105 causes the display unit 41 to display a message such as "The terminal is not compatible" so as to inform the operator that the connected information terminal 40 is not usable as an ultrasound diagnosis monitor.

Next, exemplary screens of the display unit 41 corresponding to the types of the information terminal 40 will be explained.

Figure 5A:
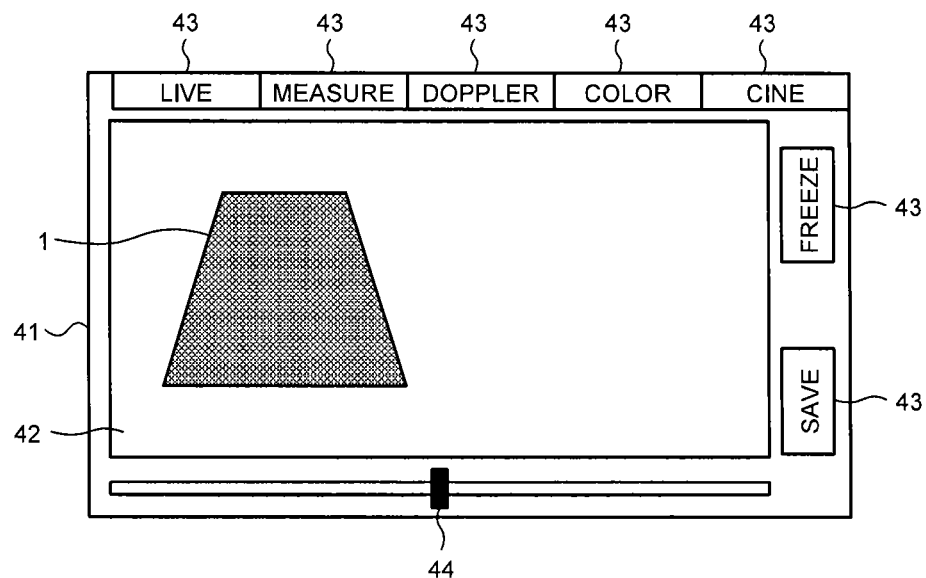
FIG. 5A and FIG. 5B are schematic drawings of an exemplary diagnosis screen on a display unit controlled by a first software component according to the first embodiment.
Figure 5B:
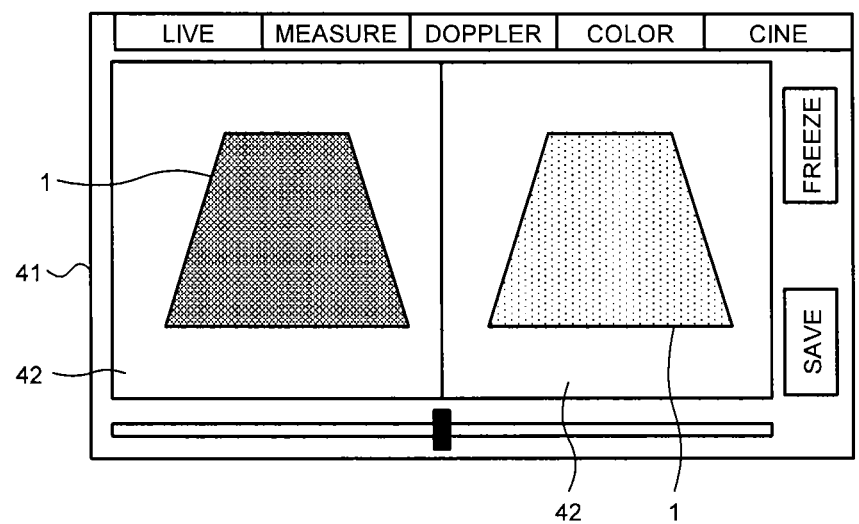

FIGS. 5A and 5B illustrate exemplary monitor displays corresponding to the situation where the information terminal 40 is a medium-sized information terminal, i.e., when the first software component controls the display/operation system. In the following sections, characteristics of the control exercised by the first software component 101 will be explained.

As shown in FIG. 5A, the display unit 41 has a diagnosis image area 42 for displaying the diagnosis image 1 in a large size, and the operation buttons 43 are provided around the diagnosis image area 42. The operation buttons 43 include buttons for changing the mode and storing data as well as a button for changing the display. When the display is changed, it is possible to cause image data in a different mode to be displayed. It is acceptable to provide an operation button 43 to "CHANGE MODE" so that the mode is sequentially changed in the order of LIVE→Measure→Doppler→Color→CINE. Alternatively, it is acceptable to cause a plurality of operation buttons 43 corresponding to the mutually-different modes to be displayed, so that the mode is directly changed when the operator has selected one of the operation buttons 43 that are displayed in a row.

It is also acceptable to provide a control bar 44 used for controlling the volume of gain control or the like, so that the control is exercised by an operation performed on the touch panel. By performing a touch operation in the diagnosis image area 42 or on the diagnosis image 1, it is possible to move a display region within the diagnosis image 1 and to enlarge or reduce the diagnosis image 1.

Further, another arrangement is also acceptable in which, every time the operator touches the diagnosis image area 42 or the diagnosis image 1, for example, the mode changes in the order of Scan→Freeze→Scan→Freeze. Yet another arrangement is also acceptable in which, when the operator performs a flick operation (i.e., while touching the screen, the operator moves the touching position across the diagnosis image 1 in left-and-right directions or up-and-down directions), the mode is changed between, for example, a color mode and a black-and-white mode. Examples of changing the mode also include changing the display region by dividing the diagnosis image area 42 into two sections (FIG. 5B). In that situation, two images in mutually-different modes may be displayed in the two areas, respectively. Alternatively, when one of the two displayed images is touched, the diagnosis image 1 displayed in the touched area may be frozen or released from a frozen state. Besides these examples, it is possible to perform other various operations by using the two areas.

In the present example, the operation buttons 43 are displayed on the outside of the diagnosis image area 42 in FIGS. 5A and 5B; however, the first embodiment is not limited to this example. It is acceptable to change the positional arrangements of the buttons and the diagnosis image area 42, as necessary. For example, the operation buttons 43 may be provided in the diagnosis image area 42. Alternatively, an area other than the diagnosis image area 42 on the display unit 41 may be used as an operation area, so that the operation buttons 43 are provided in the operation area.

Figure 6A:
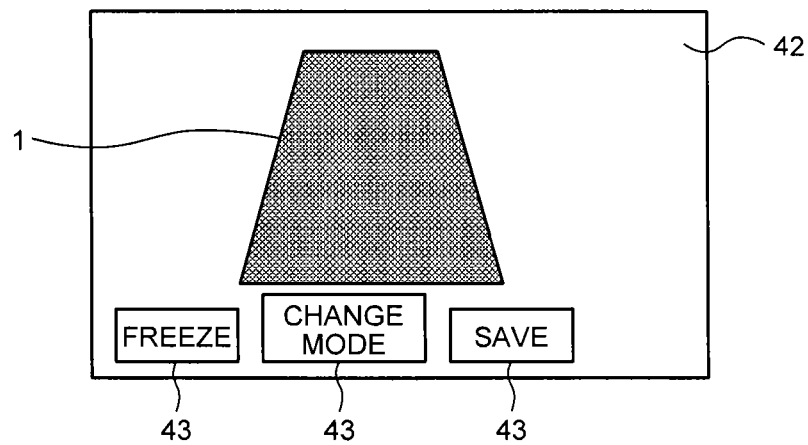
Figure 6B:
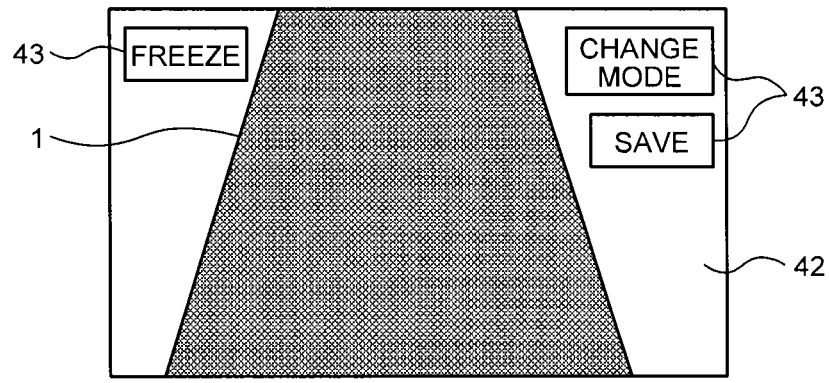

FIGS. 6A, 6B, and 6C illustrate exemplary monitor displays corresponding to the situation where the information terminal 40 is a small-sized information terminal, i.e., when the second software component 102 controls the display/operation system.

Because the display area of the display unit of a small-sized information terminal is small, it is important to display the diagnosis image in a size as large as possible so as to provide a display useful for a diagnosis procedure. For this reason, the second software component 102 exercises control in such a manner that, as shown in FIGS. 6A, 6B, and 6C, the diagnosis image area 42 is displayed on the entire screen of the display unit 41, that no particular operation area for the operation buttons 43 is provided, and that required minimum operation buttons 43 that are in a smaller quantity than the quantity of operation buttons displayed on a medium-sized information terminal are displayed in the diagnosis image area 42.

For example, an arrangement is acceptable in which, when the operator performs a touch operation in an operation-area calling region provided in a part of the display unit 41 (e.g., a blank region on the outside of the diagnosis image area 42), an operation area is temporarily displayed so as to be superimposed on the diagnosis image area 42 so that the operator can perform various types of operations. In that situation, the operation buttons 43 do not have to be displayed on the screen until the operation area is called, and also, the display of the operation area can disappear at the same time when the operation is finished.

While the control is exercised by the second software component 102, the display of the tabs used for changing the mode like those used under the control of the first software component 101 (cf. FIGS. 5A and 5B) is omitted in order to keep the display region of the diagnosis image area 42 large. Consequently, one of the operation buttons 43 serving as a "CHANGE MODE" button is used to change the mode.

Every time the "CHANGE MODE" button is operated, control is exercised so as to change the mode in the order of LIVE→Measure→Doppler→Color→CINE. Because the operation to change into each of the modes can be controlled by using one button, it is possible to save the display region of the operation buttons 43 and to keep the region assigned to the diagnosis image area 42 larger.

Another arrangement is also acceptable in which, similar to the first software component 101, when a touch operation is performed in the diagnosis image area 42, the diagnosis image 1 is frozen, enlarged, or reduced, and/or data is stored.

In the present example, the operation buttons 43 are displayed at the bottom of the diagnosis image area 42 in FIG. 6A; however, the positions of the operation buttons 43 do not necessarily have to be fixed. It is acceptable to change the positions as necessary. For example, an arrangement is acceptable in which, as shown in FIG. 6B, when the diagnosis image 1 is enlarged by performing a touch operation in the state shown in FIG. 6A, the operation buttons 43 are automatically moved to the space outside the diagnosis image 1 within the diagnosis image area 42.

When the second software component 102 exercises control so that the diagnosis image area 42 is displayed in the full size of the display unit 41, an arrangement is acceptable in which, as shown in FIG. 6C, a box 48 is displayed when the operator performs a drag operation on the diagnosis image 1 (i.e., while touching the screen, the operator continuously moves the touching position from an area in the diagnosis image 1 to another area). In that situation, another arrangement is also acceptable in which, when the operator has moved the dragged touch position to the box 48, the diagnosis image 1 is stored into a memory in the information terminal or storage on a network.

Figure 7:
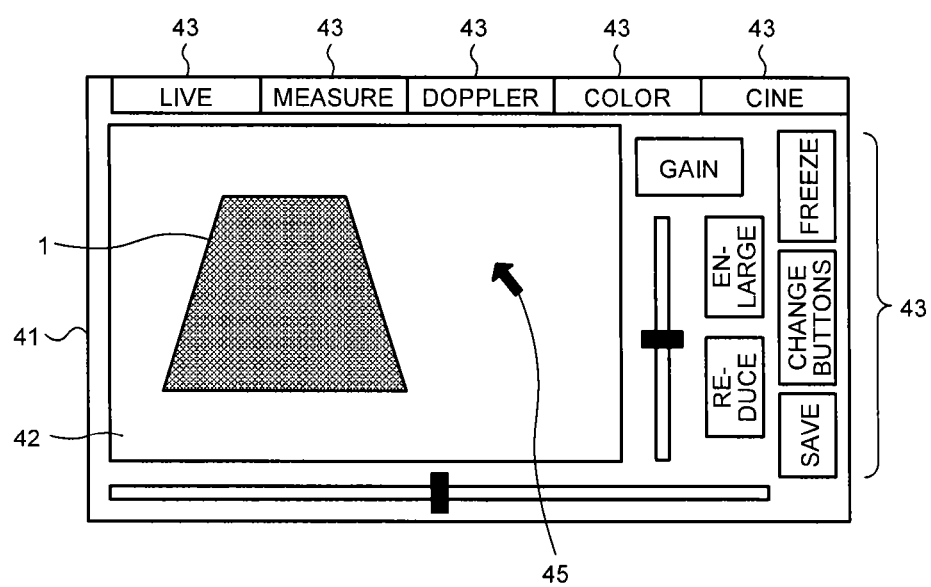
FIG. 7 is a schematic drawing of an exemplary diagnosis screen on a display unit controlled by a third software component according to the first embodiment.

FIG. 7 illustrates an exemplary monitor display corresponding to the situation where the information terminal 40 is a personal computer, i.e., when the third software component controls the display/operation system. To enable the operator to perform various types of operations (e.g., enlarging/reducing the diagnosis image 1) by using a cursor 45, a larger quantity of operation buttons are provided. When the operator operates one of the operation buttons 43 serving as a "CHANGE BUTTONS" button by using the cursor 45, the display of the operation buttons 43 is changed so that different types of operation buttons 43 are displayed.

The control exercised over the display/operation system by the third software component is different from the control exercised by the first and the second software components in that the cursor 45 is used for operating the operation buttons 43 and that a different text input screen is used. Another arrangement is also acceptable in which the third software component is configured so as to display keyboard operations in association with the control realized by the operation buttons 43, so that the operations assigned to the operation buttons 43 can be performed through operations on the keyboard.

For example, it is possible to exercise control so that the "SAVE" (data storing) process assigned to one of the operation buttons 43 is realized by pressing the "S" key of the keyboard, instead of operating the button with the cursor 45. In that situation, it is ideal to display a corresponding keyboard over each of the operation buttons 43, so as to display information such as "SAVE (S)". The display to aid the operation (e.g., "(S)") may be displayed over each of the operation buttons 43 from the beginning or may be displayed so as to appear depending on an operation performed on the keyboard or the pointing device.

Figure 8A:
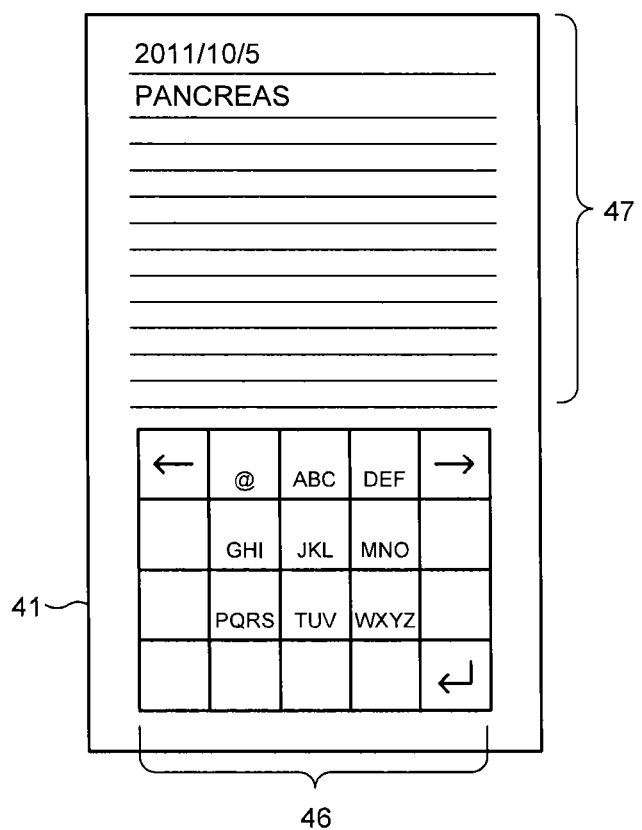
FIG. 8A, FIG. 8B and FIG. 8C are schematic drawings of an exemplary text input screen on a display unit controlled by the first to the third software components according to the first embodiment.
Figure 8B:
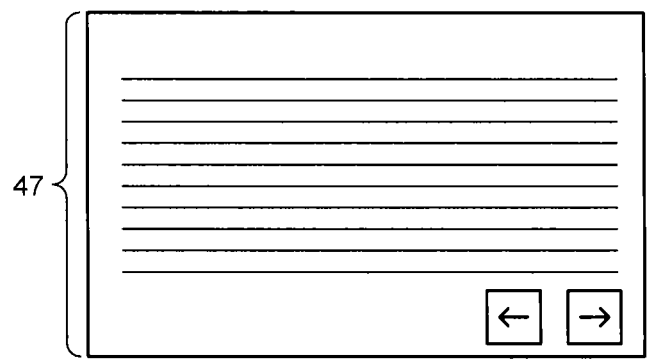
Figure 8C:
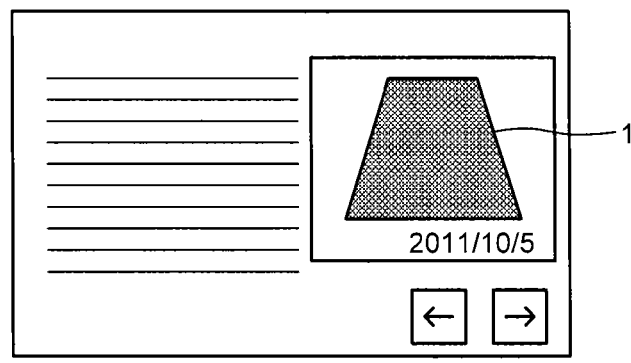

Next, a text input function controlled by the software components will be explained. In the present example, it is assumed that a text input screen is provided no matter what type of information terminal 40 is connected. Further, it is also assumed that the text input screen is called by operating one of the operation buttons 43 serving as an "INPUT TEXT" button. FIGS. 8A, 8B, and 8C are schematic drawings of exemplary text input screens controlled by the software components.

FIG. 8A illustrates a text input screen (controlled by the first software component or the second software component) corresponding to an information terminal provided with a touch panel, such as a medium-sized information terminal (e.g., a tablet terminal) or a small-sized information terminal (e.g., a smartphone). Text is input into an information input area 47 by using information input buttons 46.

In contrast, when the information terminal 40 is a terminal (e.g., a personal computer) provided with a keyboard (controlled by the third software component), text is input by using the keyboard. In that situation, when the text is input through the keyboard, there is no need to display the character buttons. Consequently, as shown in FIG. 8B, a simple screen is displayed with minimum operation buttons 43, so that the information input area 47 is displayed in a large size. Also, another arrangement is acceptable in which, as shown in FIG. 8C, the operator is able to input text, while the diagnosis image 1 is being displayed. Alternatively, yet another arrangement is also acceptable in which, while the diagnosis image area 42 is being displayed, the operator is able to input information on the inside of the diagnosis image area 42.

By performing a touch operation while the first or the second software component is used and by operating the pointing device while the third software component is used, the operator is able to input various types of information into the information input area 47, not only text but also figures like arrows.

Figure 9:
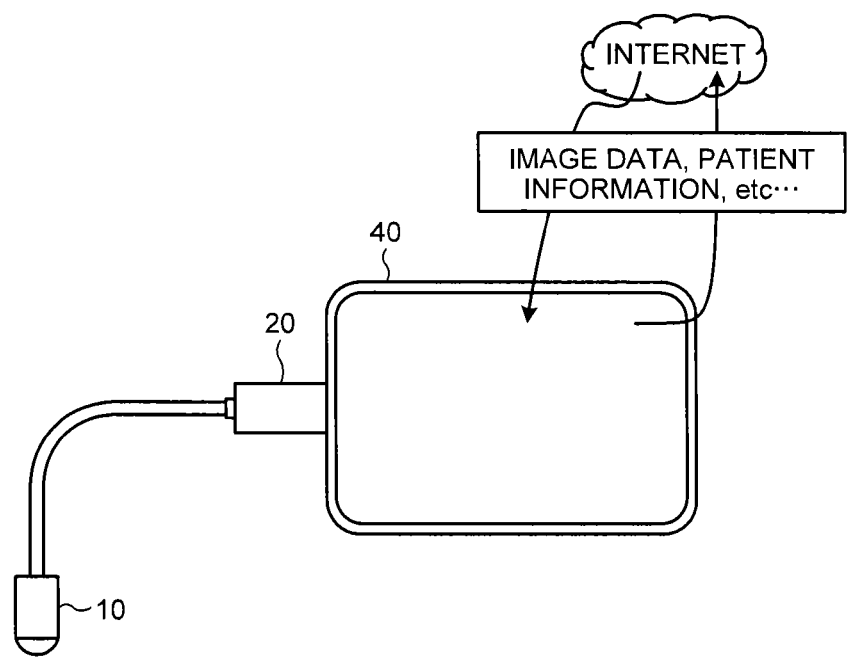
FIG. 9 is a schematic drawing illustrating how data is transmitted and received by a communication means with which an information terminal is provided according to the first embodiment.

FIG. 9 is a conceptual drawing of an example in which the information terminal 40 is provided with a communication function and is able to transmit and receive data by communicating with a server. In the present example, the "data" denotes the image data of the diagnosis image 1 or text data representing patient information. The image data of the diagnosis image 1 does not necessarily have to be that of an ultrasound image. It is possible to receive an image taken by using any other modality and to cause the received image to be displayed on the display screen. Further, the image memory 25 provided for the information terminal 40 stores therein not only the image data of the diagnosis image 1, but also text data regarding the patient information received as an input text. Further, the communication function of the information terminal 40 may be used for uploading data into the server or downloading data from the server. When the diagnosis image 1 or the patient information is stored, the data may be automatically uploaded into the server. Alternatively, another arrangement is acceptable in which the operator is able to select only necessary data after a diagnosis procedure and to upload the selected data.

Next, advantageous effects of the portable ultrasound diagnosis apparatus according to the first embodiment will be explained.

As explained above, according to the first embodiment, by simply connecting one of the various types of information terminals 40 each having a monitor to the processing unit 20, it is possible to conveniently use the display unit 41 of the information terminal 40 as the ultrasound diagnosis monitor. As a result, it is possible to separate the display monitor and the processing unit 20 from each other, and it is therefore possible to improve the two capability aspects that may conflict with each other, namely, the portability of the ultrasound diagnosis apparatus and the visibility of the display monitor. Consequently, for example, when a medical doctor visits a patient's residence to perform an ultrasound diagnosis procedure, the apparatus is easy to carry and convenient. At the same time, the monitor having excellent visibility makes it possible to perform a diagnosis procedure accurately.

Further, the portable ultrasound diagnosis apparatus according to the first embodiment is able to conveniently use a tablet terminal, a smartphone, or the like, which is very widely used these days, as a display monitor. Consequently, this feature is very useful in case of disasters and emergency. For example, if an information terminal which a medical doctor is using becomes unusable due to having a defect or running out of battery, the medical doctor is able to use a tablet terminal or a smartphone owned by his/her patient or any other person around his/her patient.

In other words, because the display screen of the display unit 41 is varied depending on the type of the information terminal 40 connected to the processing unit 20, it is possible to appropriately perform an ultrasound image diagnosis procedure with any information terminal regardless of the type of information terminal 40, while information terminals are available in abundance and in a great variety. For example, when a small-sized information terminal (e.g., a smartphone) is used as the information terminal 40, it is possible to display the diagnosis image 1 in a large size, by reducing the quantity of operation buttons 43, displaying the diagnosis image area 42 on the entire screen of the display unit 41, and providing the operation buttons 43 in a movable manner.

As another example, if the information terminal 40 has a gyro sensor installed therein, because it is possible to perform various types of operations by using the gyro sensor, there is no need to display the operation buttons 43 for those operations, and it is therefore possible to display the diagnosis image 1 in a larger size. In that situation, the operation of changing the mode may be performed by, for example, shaking the information terminal 40.

Another arrangement is also acceptable in which movements (gestures) of the operator are recognized by a camera provided on the front side of the information terminal 40, so that the cursor is moved or the buttons are operated according to the recognized movements. In that situation, with a small-sized information terminal, it is possible to display an operation screen that is more suitable for the operator's circumstances, in accordance with the information terminal being connected, e.g., to display the diagnosis image 1 on the display unit 41 in a larger size by reducing the quantity of operation buttons 43 and allowing the operator to perform the various types of operations by gestures.

When information has been input on the text input screen, which is displayed when the screen display of the information terminal 40 is changed, it is possible to store the input data into the information terminal 40 together with the diagnosis image 1, as the patient information or as an annotation (a comment) related to the diagnosis image 1. Further, it is also possible to store the input data into a server by using the communication function of the information terminal 40. Also, because it is possible to browse the stored data at hospitals and the like, this feature is useful for remote medical services.

When the display screen is divided into two sections or when the information terminal 40 is provided with two display screens, it is also possible to display a stored image on one screen while displaying the diagnosis image 1 on the other screen, so as to compare the images easily. With this arrangement, it is possible to check progress of symptoms by, for example, making a comparison with an image from a previously-performed diagnosis procedure. The stored image may be an ultrasound diagnosis image of the patient taken in the past or may be an ultrasound diagnosis image showing a sample case of the disease. The displayed images are not limited to ultrasound diagnosis images and may be images taken by using any other modality such as Computed Tomography (CT) apparatuses, Magnetic Resonance Imaging (MRI) apparatuses, and the like. It is possible to perform a more advanced diagnosis procedure by using different images in different circumstances. Further, it is also acceptable to display an item other than images and patient information on one of the display areas. For example, it is possible to support an operator who is not familiar with ultrasound diagnosis procedures by displaying a method for properly operating the ultrasound probe 10.

Further, another arrangement is acceptable in which the image processing circuit 24 configured to generate the image data is omitted from the processing unit 20, so that the function of the image processing circuit 24 is realized by the information terminal 40. In that situation, the function (the image generating function) of the image processing circuit 24 to generate the image data is incorporated as a part of the functions of the first to the third software components, so that the information terminal 40 having the software components installed therein realizes the processing. When the information terminal 40 is to execute the image generating function, the connecting unit 30 transmits the digital signals processed by the A/D converter 23, instead of the image data, to the information terminal 40. With this arrangement, it is possible to further simplify the calculating process performed the processing unit 20. Consequently, it is possible to make the processing unit 20 more compact.

The advantage effects of the first embodiment described above can be summarized as follows: Because the diagnosis screen is provided in accordance with the information terminal 40 connected to the processing unit 20, it is possible to use any type of information terminal 40 as the ultrasound diagnosis monitor. It is therefore possible to improve both the portability and the operability. Further, even a layperson who is not a medical doctor is able to perform an ultrasound diagnosis procedure by using a device on hand such as a tablet terminal or a smartphone and is also able to transmit diagnosis data obtained by using the device to a hospital. Consequently, in emergency, it is possible to, for example, immediately perform an ultrasound diagnosis procedure before an ambulance arrives. Thus, this feature is also useful in critical emergency situations.

Further, although a tablet terminal provided with a monitor was used as an example of the information terminal 40 configured to display the ultrasound diagnosis image, the exemplary embodiments are not limited to this example. For example, another arrangement is acceptable in which the information terminal 40 has no display monitor, but a retinal scan display configured to directly radiate light onto the retina and to project a picture thereon is used, so that an ultrasound diagnosis image can be displayed on the retina. In that situation, the ultrasound probe 10 or the like is provided with buttons and the like used for performing various types of operations. When the ultrasound probe 10 is provided with the buttons used for performing the operations, it is possible to operate the ultrasound probe 10 during a diagnosis procedure and to perform other operations such as to change the diagnosis image 1 or the mode with one hand. As a result, because the other hand is free, the operator is able to perform other various actions that can be realized with one hand during the diagnosis procedure (e.g., perform a diagnosis procedure while holding the patient's hand). With this arrangement, it is possible to make the patient feel more secure during the diagnosis procedure.

An overview of a portable ultrasound diagnosis apparatus according to a second embodiment will be explained, with reference to FIG. 10. The second embodiment is different from the first embodiment in terms of the method for controlling the information terminal. Other constituent elements are not different.

Figure 10:
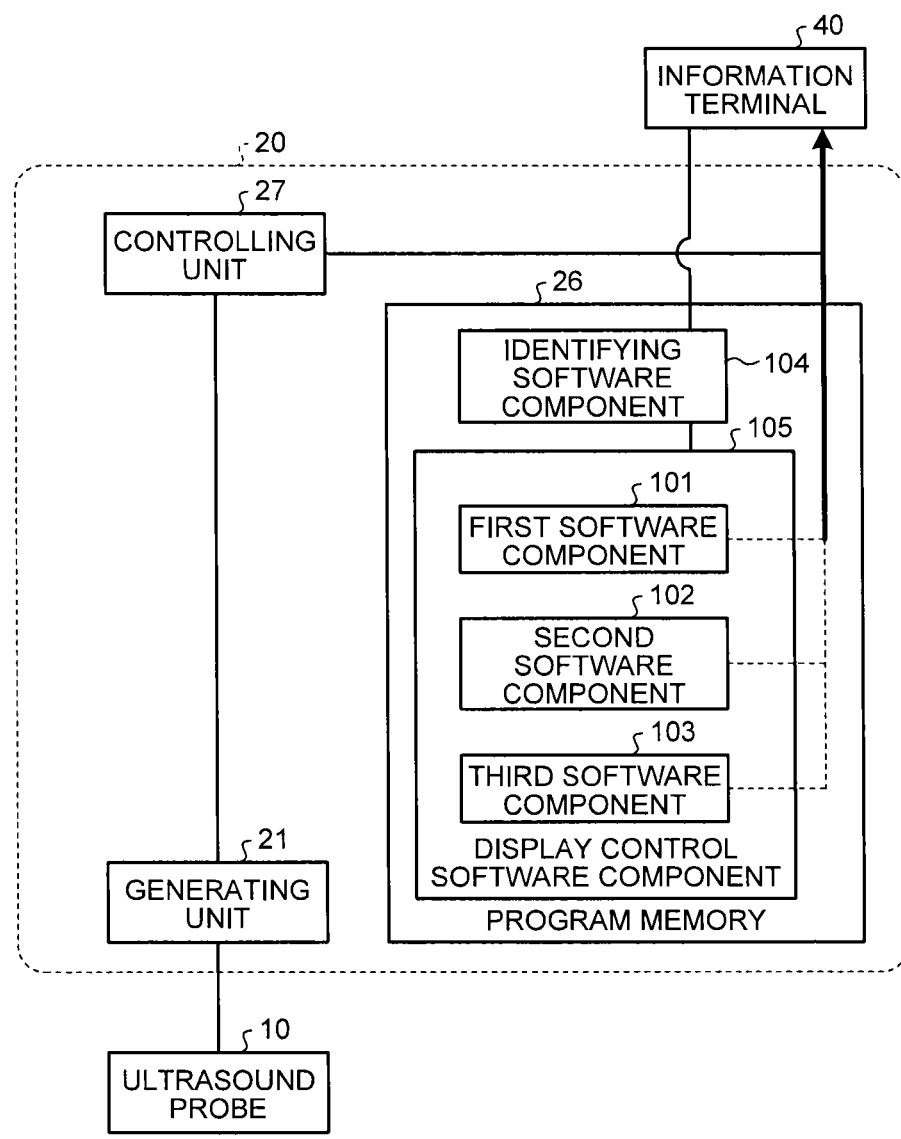
FIG. 10 is a block diagram of an overall configuration according to a second embodiment.

FIG. 10 is a block diagram illustrating a manner in which the identifying software component 104 provided in the program memory 26 specifies an appropriate software component from among the first to the third software components included in the display control software component 105, on the basis of a result of an identifying process obtained by the identifying software component 104, so that the specified software component is automatically installed on the information terminal 40 side by the display control software component 105, the information terminal 40 being connected to the processing unit 20.

In the same manner as described in the first embodiment, the identifying software component 104 provided in the program memory 26 identifies the information about the information terminal 40 connected to the processing unit 20. On the basis of the result of the identifying process, the identifying software component 104 specifies a software component suitable for the information terminal 40 connected to the processing unit 20, from among the first to the third software components. After that, the display control software component 105 causes the specified software component to be installed in the information terminal 40. In FIG. 10, the dotted lines connecting the first software component 101, the second software component 102, and the third software component 103 together indicate that only one of the software components can be installed in the information terminal 40. The identifying software component 104 may be provided in the controlling unit 27.

When the installation of the software component has been finished, the information terminal 40 is usable as a display monitor of the ultrasound diagnosis apparatus and is capable of displaying picture data obtained by the generating unit 21. Operation buttons (not shown) provided for the processing unit 20 are used on minimal occasions such as when connecting the information terminal 40 to the connecting unit 30, when the installation has finished, and when the information terminal 40 is disconnected from the connecting unit 30. The operation buttons do not need to be used during the process of installing the software component suitable for the information terminal 40.

If the information terminal 40 connected to the processing unit 20 has already installed therein a software component (the first, the second, or the third software component) used for performing a diagnosis procedure, there is no need to install a new software component from the processing unit 20. Thus, a diagnosis procedure is performed immediately after the processing unit 20 and the information terminal 40 are connected to each other. The method for controlling the display/operation system implemented by each of the software components is the same as that described in the first embodiment.

Next, an operation performed the portable ultrasound diagnosis apparatus according to the second embodiment will be explained.

Figure 11:
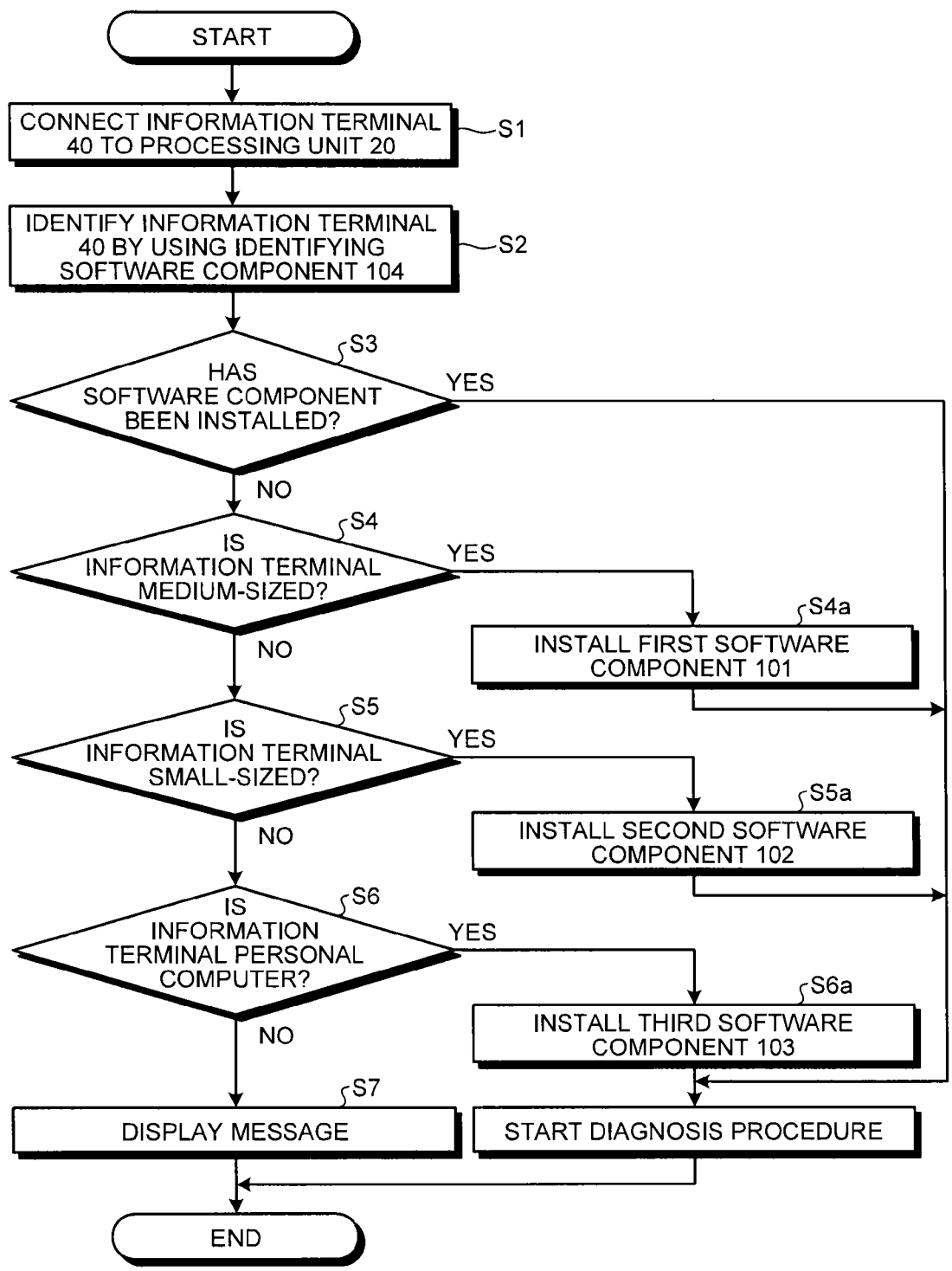
FIG. 11 is a flowchart illustrating a flow of a series of operations according to the second embodiment.

FIG. 11 is a flowchart according to the second embodiment. The method used for determining whether the information terminal 40 is a medium-sized information terminal, a small-sized information terminal, or a personal computer is the same as that described in the first embodiment.

At step S1, the operator connects the information terminal 40 to the processing unit 20. The information terminal 40 may directly be connected to the connecting unit 30 of the processing unit 20. Alternatively, if the information terminal 40 includes a wireless function, the operator operates the processing unit 20 or the information terminal 40 so as to start wireless communication.

At step S2, the identifying software component 104 included in the processing unit 20 identifies the information about the information terminal 40, which is connected to the processing unit 20 as a result of step S1.

At step S3, on the basis of the information obtained at step S2, the identifying software component 104 judges whether the information terminal 40 connected to the processing unit 20 has installed therein a software component (one of the first to the third software components) used for performing a diagnosis procedure. If the software component has been installed (step S3: Yes), the installed software component is run, so that the installed software component starts controlling the display/operation system of the information terminal 40, and the process proceeds to the diagnosis procedure. If the software component has not been installed (step S3: No), the process proceeds to step S4.

At step S4, on the basis of the information obtained at step S2, the identifying software component 104 judges whether the information terminal 40 is a medium-sized information terminal by determining the size of the display unit 41 of the information terminal 40 connected to the processing unit 20 and judging whether a touch panel is provided or not that can be used for performing an operation on the diagnosis image 1 displayed on the display unit 41. If the information terminal 40 is a medium-sized information terminal (step S4: Yes), the process proceeds to step S4a. If the information terminal 40 is not a medium-sized information terminal (step S4: No), the process proceeds to step S5.

At step S4a, the identifying software component 104 specifies the first software component 101. On the basis of the specified result, the display control software component 105 causes the first software component 101 to be installed in the information terminal 40 connected to the processing unit 20. The installed first software component 101 thus controls the display/operation system of the information terminal 40, and the process proceeds to the diagnosis procedure.

At step S5, on the basis of the information obtained at step S2, the identifying software component 104 judges whether the information terminal 40 is a small-sized information terminal by determining the size of the display unit 41 of the information terminal 40 connected to the processing unit 20 and judging whether a touch panel is provided or not that can be used for performing an operation on the diagnosis image 1 displayed on the display unit 41. If the information terminal 40 is a small-sized information terminal (step S5: Yes), the process proceeds to step S5a. If the information terminal 40 is not a small-sized information terminal (step S5: No), the process proceeds to step S6.

At step S5a, the identifying software component 104 specifies the second software component 102. On the basis of the specified result, the display control software component 105 causes the second software component 102 to be installed in the information terminal 40 connected to the processing unit 20. The installed second software component 102 thus controls the display/operation system of the information terminal 40, and the process proceeds to the diagnosis procedure.

At step S6, on the basis of the information obtained at step S4 or S5 indicating whether a touch panel and/or a keyboard or a pointing device is provided, the identifying software component 104 checks to see whether the information terminal 40 is a personal computer. If the information terminal 40 is a personal computer (step S6: Yes), the process proceeds to step S6a. If the information terminal 40 is not a personal computer (step S6: No), the process proceeds to step S7.

At step S6a, the identifying software component 104 specifies the third software component 103. On the basis of the specified result, the display control software component 105 causes the third software component 103 to be installed in the information terminal 40 connected to the processing unit 20. The installed third software component 103 thus controls the display/operation system of the information terminal 40, and the process proceeds to the diagnosis procedure.

At step S7, the display control software component 105 causes the display unit 41 to display a message such as "The terminal is not compatible" so as to inform the operator that the connected information terminal 40 is not usable as an ultrasound diagnosis monitor.

In the following sections, advantageous effects of the portable ultrasound diagnosis apparatus according to the second embodiment will be explained.

According to the second embodiment, it is possible to provide the portable ultrasound diagnosis apparatus having excellent visibility and portability, like in the first embodiment. Further, because it is possible to install the software component corresponding to the information terminal 40 into the information terminal 40, it is possible to perform a diagnosis procedure immediately when the information terminal 40 that has already installed the software component therein is used again. In addition, because the various types of control are exercised on the information terminal 40 side, the information terminal 40 does not necessarily have to be connected to the processing unit 20 when the patient information is input and when communication with a server is performed. Consequently, by disconnecting the processing unit 20 and the information terminal 40 from each other after the diagnosis procedure has been finished, it is possible to perform operations on the various types of data after the diagnosis procedure, while excellent portability and operability are maintained.

An overview of a portable ultrasound diagnosis apparatus according to a third embodiment will be explained, with reference to FIG. 12.

The third embodiment is different from the first and the second embodiments in terms of the method for controlling the information terminal 40. In the third embodiment, the identifying software component 104 does not have to be provided on the processing unit 20 side. A software component installed in the information terminal 40 is configured to identify the information terminal 40. Other constituent elements are not different.

Figure 12:
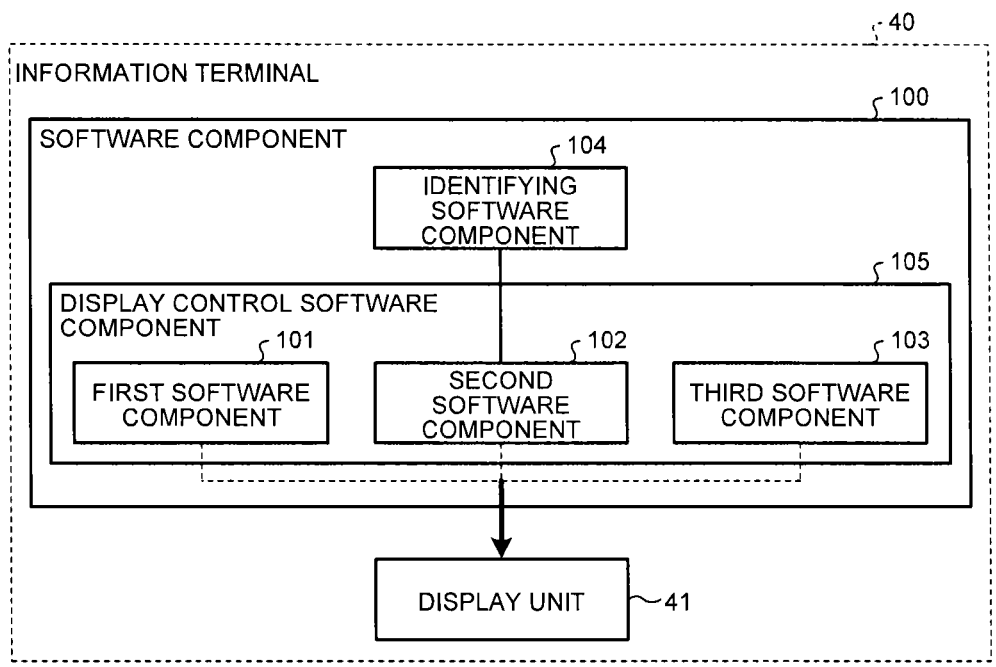
FIG. 12 is a block diagram of a method for controlling the information terminal according to a third embodiment.
Figure 13:
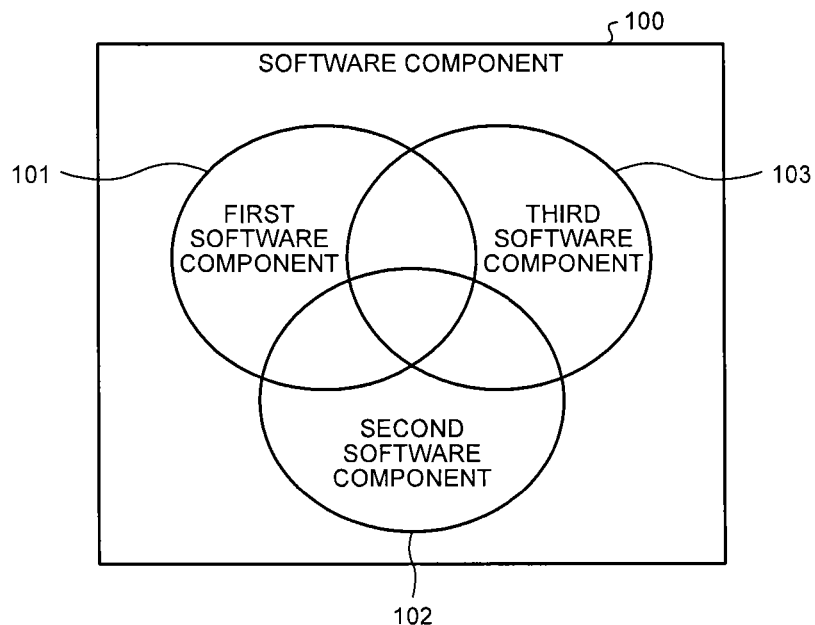
FIG. 13 is a Venn diagram illustrating a relationship among software components according to the third embodiment.

FIG. 12 is a schematic drawing for explaining a manner in which a software component 100 provided in the processing unit 20 is automatically installed on the information terminal 40 side, the information terminal 40 being connected to the processing unit 20, and further, the installed software component 100 controls the display/operation system corresponding to the information terminal 40. In other words, the software component 100 is a software component that includes the first to the third software components described in the first and the second embodiments (FIG. 13). The third embodiment is different from the second embodiment in that the software component 100 is installed at first into the information terminal 40. FIG. 13 is a Venn diagram illustrating an exemplary relationship among the software component 100 and the first to the third software components. Each of the first to the third software components is indicated with a circle. Each circle has intersection portions that overlap with one or both of the other circles and has a portion that does not overlap. This means that, for example, because the control exercised by the first software component 101 is different from the control exercised by the second software component 102 in that a large quantity of operation buttons 43 are present on the display unit 41 (see FIGS. 5A to 6C), the portion that exercises this type of control is such a portion of the circle of the first software component 101 shown in FIG. 13 that does not overlap with the other circles.

After the software component 100 has been installed, each of the software components (the first to the third software components) corresponding to the connected information terminal 40 controls the display/operation system.

Figure 14:
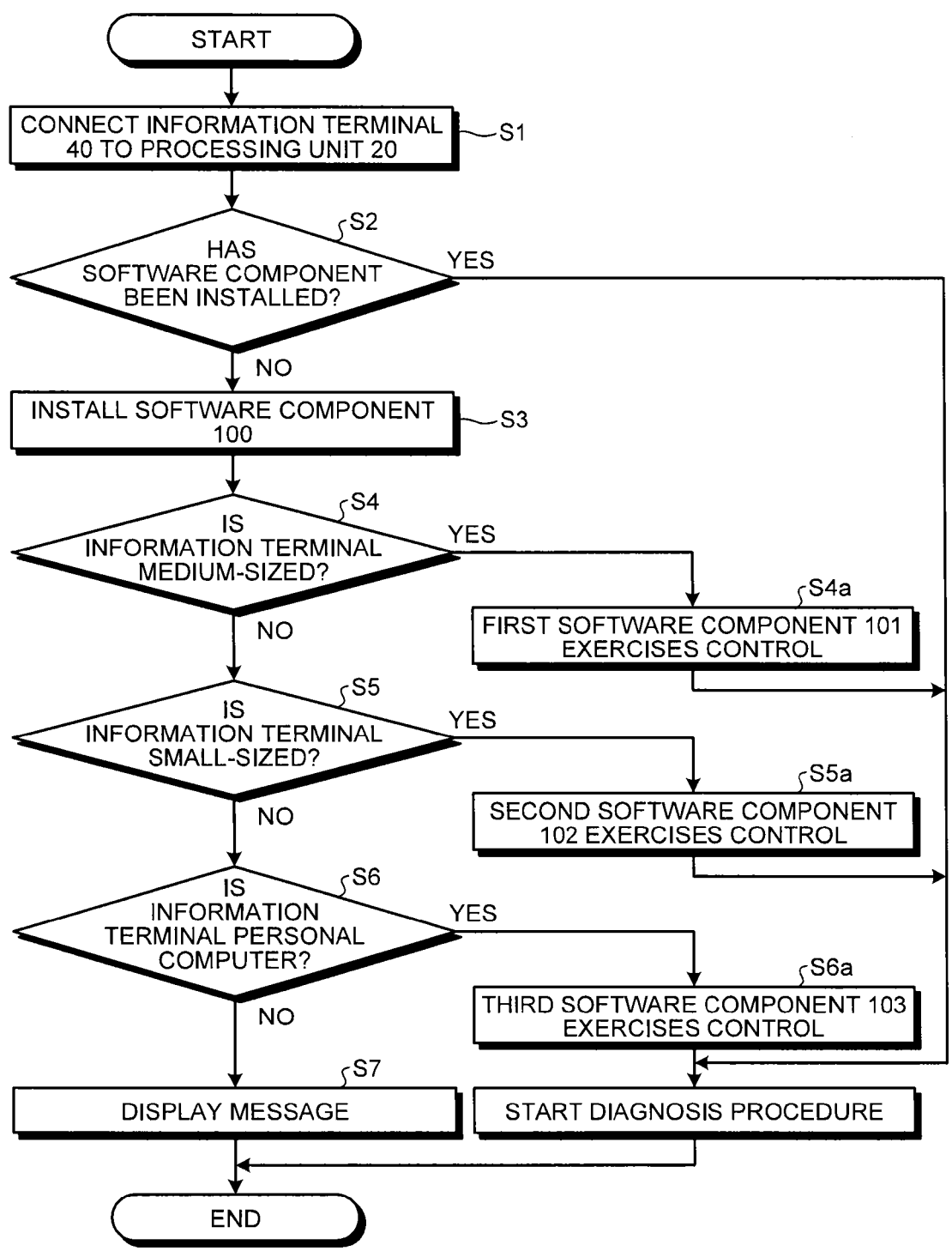
FIG. 14 is a flowchart illustrating a flow of a series of operations according to the third embodiment.

A flow of the procedure will be explained, with reference to the flowchart in FIG. 14. The method used for determining whether the information terminal 40 is a medium-sized information terminal, a small-sized information terminal, or a personal computer is the same as that described in the first and the second embodiments.

At step S1, the operator connects the information terminal 40 to the processing unit 20.

At step S2, the operator judges whether the information terminal 40 connected to the processing unit 20 has installed therein the software component 100 or the first to the third software components used for performing a diagnosis procedure. If the software component 100 or the software components have been installed (step S2: Yes), the information terminal 40 runs the installed software component so as to control the display/operation system, and the process proceeds to the diagnosis procedure. If none of the software components has been installed (step S2: No), the process proceeds to step S3.

At step S3, an installation control software component (not shown) provided on the processing unit 20 side installs the software component 100 into the information terminal 40 connected to the processing unit 20.

At step S4, the identifying software component 104 included in the software component 100 installed at step S3 identifies the information about the information terminal 40 and judges, on the basis of the identified information, whether the information terminal 40 is a medium-sized information terminal by determining the size of the display unit 41 and judging whether a touch panel is provided or not that can be used for performing an operation on the diagnosis image 1 displayed on the display unit 41. If the information terminal 40 is a medium-sized information terminal (step S4: Yes), the process proceeds to step S4a. If the information terminal 40 is not a medium-sized information terminal (step S4: No), the process proceeds to step S5.

At step S4a, the display control software component 105 included in the software component 100 installed in the information terminal 40 causes the first software component 101 to control the display/operation system of the information terminal 40 connected to the processing unit 20. The process then proceeds to the diagnosis procedure.

At step S5, the identifying software component 104 included in the software component 100 installed at step S3 identifies the information about the information terminal 40 and judges whether the information terminal 40 is a small-sized information terminal by determining the size of the display unit 41 and judging whether a touch panel is provided or not that can be used for performing an operation on the diagnosis image 1 displayed on the display unit 41. If the information terminal 40 is a small-sized information terminal (step S5: Yes), the process proceeds to step S5a. If the information terminal 40 is not a small-sized information terminal (step S5: No), the process proceeds to step S6.

At step S5a, the display control software component 105 included in the software component 100 installed in the information terminal 40 causes the second software component 102 to control the display/operation system of the information terminal 40 connected to the processing unit 20. The process then proceeds to the diagnosis procedure.

At step S6, on the basis of the information obtained at step S4 or S5 indicating whether a touch panel and/or a keyboard or a pointing device is provided, the identifying software component 104 checks to see whether the information terminal 40 is a personal computer. If the information terminal 40 is a personal computer (step S6: Yes), the process proceeds to step S6a. If the information terminal 40 is not a personal computer (step S6: No), the process proceeds to step S7.

At step S6a, the display control software component 105 included in the software component 100 installed in the information terminal 40 causes the third software component 103 to control the display/operation system of the information terminal 40 connected to the processing unit 20. The process then proceeds to the diagnosis procedure.

At step S7, the display control software component 105 causes the display unit 41 to display a message such as "The terminal is not compatible" so as to inform the operator that the connected information terminal 40 is not usable as an ultrasound diagnosis monitor. In this situation, according to the third embodiment, the software component 100 automatically causes one of the first to the third software components to exercise control corresponding to the information terminal 40. However, another arrangement is also acceptable in which the software component 100 has a changing function so as to be able to change the type of the controlling software component, so that the operator is able to make a change to an arbitrary software component on the display screen.

Next, advantageous effects of the portable ultrasound diagnosis apparatus according to the third embodiment will be explained.

According to the third embodiment, regardless of the type of the information terminal 40 connected to the processing unit 20, the same software component 100 including the first to the third software components is installed into the information terminal 40. Consequently, it is possible to select the software component to be used, according to the status of use and circumstances of the operator. For example, even if the information terminal 40 is a medium-sized information terminal, it is possible to use a display/operation system controlled by the second software component 102. With this arrangement, it is possible to display the diagnosis image 1 in a larger size and to improve the visibility.

As explained above, according to the first to the third embodiments, it is possible to provide a portable ultrasound diagnosis apparatus that is able to improve both the visibility and the portability.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A portable ultrasound diagnosis apparatus comprising:
an ultrasound probe configured to transmit and receive an ultrasound wave to and from a subject;
a processing unit being connected to the ultrasound probe and including a generating unit configured to generate image data of the subject on a basis of an ultrasound signal received by the ultrasound probe;
a display controlling unit configured to exercise control so as to cause the image data to be displayed by an information terminal being connected to the processing unit and having a display unit; and an identifying unit configured to perform an identifying process on a basis of identification information that indicates a display size of the display unit of the information terminal, wherein the identifying unit is configured to perform the identifying process by comparing the display size of the display unit of the information terminal with a threshold value to classify the information terminal into one of a plurality of types of information terminals, and the display controlling unit exercises a display control in accordance with the information terminal connected to the processing unit, by varying a size of a diagnosis image area displayed on the display unit relative to the display size of the display unit in accordance with a result of the identifying process by the identifying unit.

2. A portable ultrasound diagnosis apparatus comprising:

an ultrasound probe configured to transmit and receive an ultrasound wave to and from a subject;

a processing unit being connected to the ultrasound probe and including a generating unit configured to generate image data of the subject on a basis of an ultrasound signal received by the ultrasound probe;

a display controlling unit configured to exercise control so as to cause the image data to be displayed by an information terminal being connected to the processing unit; and an identifying unit configured to perform an identifying process on a basis of identification information that indicates a display size of a display unit of the information terminal, wherein the identifying unit is configured to perform the identifying process by comparing the display size of the display unit of the information terminal with a threshold value to classify the information terminal into one of a plurality of types of information terminals, and the display controlling unit exercises control so that a display button configured to receive an operation performed on the display unit changes in accordance with the type of the information terminal, on a basis of a result of the identifying process by the identifying unit.

3. The portable ultrasound diagnosis apparatus according to claim 2, wherein the display controlling unit is further configured to exercise control so as to move the display button arranged in a first position to a second position that is on the display unit and is different from the first position, in accordance with either a size or a position of a diagnosis image area.

4. The portable ultrasound diagnosis apparatus according to claim 2, wherein the display controlling unit is further configured to exercise control so that either a quantity or a type of a display button configured to receive an operation performed on the display unit changes in accordance with the type of the information terminal, on a basis of the result of the identifying process by the identifying unit.

5. The portable ultrasound diagnosis apparatus according to claim 3, wherein the display controlling unit is further configured to exercise control so that either a quantity or a type of a display button configured to receive an operation performed on the display unit changes in accordance with the type of the information terminal, on a basis of the result of the identifying process by the identifying unit.

6. The portable ultrasound diagnosis apparatus according to claim 1, wherein the display controlling unit is further configured to exercise control so that either a quantity or a type of a display button configured to receive an operation performed on the display unit changes in accordance with the type of the information terminal, on a basis of the result of the identifying process by the identifying unit.

7. The portable ultrasound diagnosis apparatus according to claim 1, wherein the display controlling unit is further configured to divide the diagnosis image area into two sections and exercise control so that a diagnosis image is displayed in each of the sections, on the basis of the identifying process by the identifying unit.

8. The portable ultrasound diagnosis apparatus according to claim 1, wherein if it has been determined, on the basis of the result of the identifying process by the identifying unit, that the information terminal has a gyro sensor installed therein, the display controlling unit is further configured to exercise control so that one or more display buttons configured to receive an operation performed on the display unit are displayed in a smaller quantity on the display unit than a quantity of display buttons provided for an information terminal that has no gyro sensor installed therein.

9. The portable ultrasound diagnosis apparatus according to claim 1, wherein if it has been determined, on the basis of the result of the identifying process by the identifying unit, that the information terminal has installed therein a camera configured to detect a gesture, the display controlling unit is further configured to exercise control so that one or more display buttons configured to receive an operation performed on the display unit are displayed in a smaller quantity on the display unit than a quantity of display buttons provided for an information terminal that has no such camera installed therein.

10. The portable ultrasound diagnosis apparatus according to claim 1, further comprising: a storage unit configured to store therein a plurality of software components configured to control the information terminal, wherein the display controlling unit is further configured to control the information terminal in accordance with the result obtained by the identifying unit, by selecting at least one of the plurality of software components in accordance with the result of the identifying process by the identifying unit and causing the selected software component to be installed in the information terminal.

11. The portable ultrasound diagnosis apparatus according to claim 1, wherein the identifying unit is further configured to determine whether one of a touch panel, a keyboard, and a pointing device is present with respect to the information terminal.

12. The portable ultrasound diagnosis apparatus according to claim 1, wherein the plurality of types of information terminals include a medium-sized type, a small-sized type, and a personal computer type, and the medium-sized type, the small-sized type, and the personal computer type are different from each other.

* * * * *